(12) United States Patent
Biedermann et al.

(10) Patent No.: US 12,714,482 B2
(45) Date of Patent: Aug. 25, 2026

(54) POLYAXIAL BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Achim Schünemann, VS-Mühlhausen (DE); Dimosthenis Dandanopoulos, VS-Schwenningen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 19/550,980

(22) Filed: Feb. 26, 2026

(65) Prior Publication Data

US 2026/0191572 A1 Jul. 9, 2026

Related U.S. Application Data

(63) Continuation of application No. 18/093,271, filed on Jan. 4, 2023, now Pat. No. 12,564,431, which is a (Continued)

(30) Foreign Application Priority Data

Aug. 11, 2014 (EP) .................................... 14180588

(51) Int. Cl.

| | |
|---|---|
| ***A61B 17/86*** | (2006.01) |
| ***A61B 17/68*** | (2006.01) |
| ***A61B 17/70*** | (2006.01) |

(52) U.S. Cl.

CPC .......... *A61B 17/8605* (2013.01); *A61B 17/68* (2013.01); *A61B 17/7037* (2013.01); *A61B 17/8685* (2013.01); *A61B 17/7002* (2013.01)

(58) Field of Classification Search

CPC . A61B 17/8605; A61B 17/68; A61B 17/7037; A61B 17/8685; A61B 17/002

See application file for complete search history.

(56) References Cited

U.S. PATENT DOCUMENTS

| | | | |
|---|---|---|---|
| 5,716,356 | A | 2/1998 | Biedermann et al. |
| 8,075,603 | B2 | 12/2011 | Hammill et al. |

(Continued)

FOREIGN PATENT DOCUMENTS

| | | | |
|---|---|---|---|
| CN | 1578645 | A | 2/2005 |
| CN | 1654026 | A | 8/2005 |

(Continued)

OTHER PUBLICATIONS

Extended European Search Report issued by the EPO for EP 14180588.7 on Feb. 27, 2015 (6 pages).

*Primary Examiner* — Sameh R Boles

(74) *Attorney, Agent, or Firm* — Womble Bond Dickinson (US) LLP

(57) ABSTRACT

A polyaxial bone anchoring device includes a receiving part having a longitudinal axis, a channel for receiving a rod, and an accommodation space for pivotably holding a head of a bone anchoring element, and a pressure member configured to be positioned in the receiving part and to exert pressure onto the head to lock the head in the receiving part. The pressure member includes a pressure exerting surface and a deformable portion having a free end, wherein the deformable portion is configured to assume at least a first configuration and a second configuration. The polyaxial bone anchoring device further includes a locking member configured to be inserted into the channel and to exert a force onto the deformable portion. When the head and the pressure member and the locking member are in the receiving part, the free end of the deformable portion is supported in the receiving part, and the locking member is movable in the (Continued)

channel along the longitudinal direction in such a manner that the locking member first contacts the deformable portion and exerts a force onto the deformable portion to bring the deformable portion from the first configuration into the second configuration thereby locking the head. Thereafter the locking member comes into contact with the rod and locks the rod.

19 Claims, 8 Drawing Sheets

Related U.S. Application Data continuation of application No. 16/950,723, filed on Nov. 17, 2020, now Pat. No. 11,576,708, which is a continuation of application No. 16/194,995, filed on Nov. 19, 2018, now Pat. No. 10,864,030, which is a continuation of application No. 14/822,583, filed on Aug. 10, 2015, now Pat. No. 10,159,519.

(60) Provisional application No. 62/035,666, filed on Aug. 11, 2014.

(56) References Cited

U.S. PATENT DOCUMENTS

| | | | |
|---|---|---|---|
| 8,088,152 | B2 | 1/2012 | Schumacher |
| 9,364,266 | B2 | 6/2016 | Biedermann et al. |
| 9,480,517 | B2 | 11/2016 | Jackson et al. |
| 9,924,971 | B2 | 3/2018 | Biedermann et al. |
| 10,058,367 | B2 | 8/2018 | Biedermann et al. |
| 11,333,192 | B1 | 5/2022 | Lentner et al. |
| 11,751,916 | B2 | 9/2023 | Jackson et al. |
| 2003/0158552 | A1 | 8/2003 | Jeon et al. |
| 2004/0225289 | A1 | 11/2004 | Biedermann et al. |
| 2005/0154391 | A1 | 7/2005 | Doherty et al. |
| 2007/0093827 | A1 | 4/2007 | Warnick |
| 2008/0269809 | A1 | 10/2008 | Garamszegi |
| 2008/0294202 | A1 | 11/2008 | Peterson et al. |
| 2009/0062865 | A1 | 3/2009 | Schumacher |
| 2009/0254125 | A1 | 10/2009 | Predick |
| 2010/0030279 | A1 | 2/2010 | Flynn et al. |
| 2012/0046699 | A1 | 2/2012 | Jones et al. |
| 2012/0232598 | A1 | 9/2012 | Hestad et al. |
| 2012/0253408 | A1 | 10/2012 | Timm |
| 2013/0096622 | A1 | 4/2013 | Biedermann et al. |
| 2013/0150852 | A1 | 6/2013 | Shluzas et al. |
| 2013/0197586 | A1 | 8/2013 | Matthis et al. |
| 2013/0338721 | A1 | 12/2013 | Biedermann et al. |
| 2013/0345761 | A1 | 12/2013 | Biedermann et al. |
| 2015/0032162 | A1* | 1/2015 | Biedermann ...... A61B 17/7035 606/278 |
| 2015/0201972 | A1 | 7/2015 | Doubler et al. |

FOREIGN PATENT DOCUMENTS

| | | | |
|---|---|---|---|
| CN | 1784181 | A | 6/2006 |
| CN | 103222890 | A | 7/2013 |
| EP | 1222899 | A2 | 7/2002 |
| EP | 1726264 | A1 | 11/2006 |
| EP | 2022424 | A1 | 2/2009 |
| EP | 2 070 485 | A1 | 6/2009 |
| EP | 2 221 012 | A1 | 8/2010 |
| EP | 2 687 171 | A1 | 1/2014 |
| EP | 2 687 172 | B1 | 3/2015 |
| JP | 2009-142655 | A | 7/2009 |
| JP | 2013-255794 | | 12/2013 |
| JP | 2014-018664 | A | 2/2014 |
| WO | WO 2006/116437 | A2 | 11/2006 |

* cited by examiner 81
8
84
100
C
77a
78a
77
78
74
7
57
5a
58
5
51
5b
6
61
4
3
1
2

C
8
100
54
5
1
2

Fig. 3
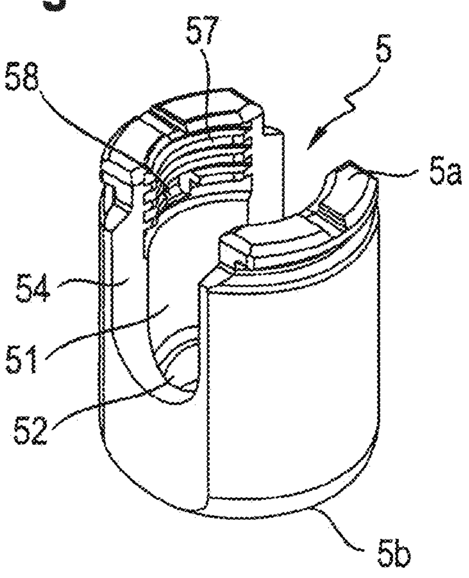
Fig. 4
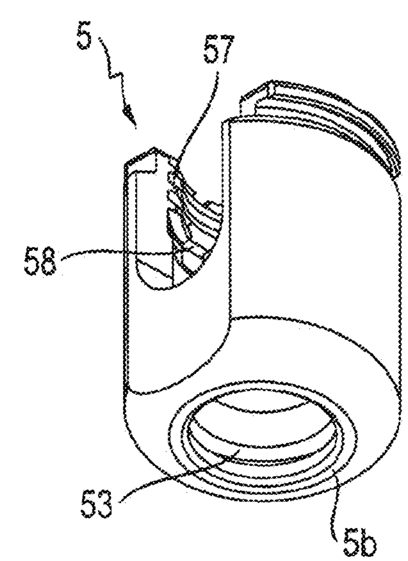
5
54
5a
A
A
Fig. 5
Fig. 6
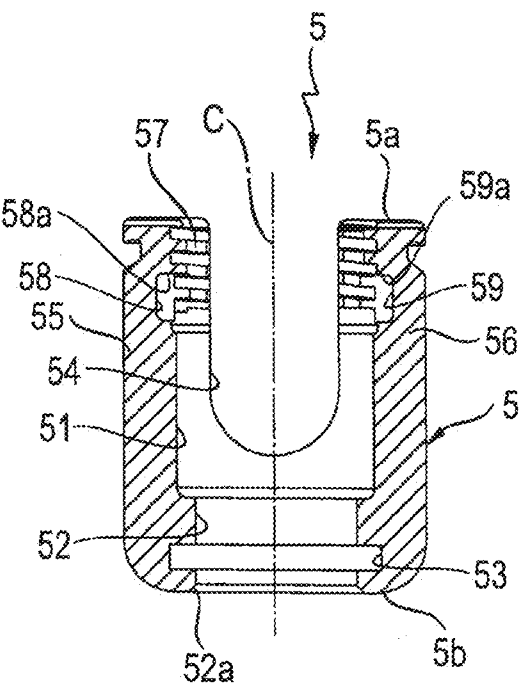

C
7
77a
77c
7a
76
75
78c
78a
α
78
77
77b
72
74
7a
78b
73
71
7b 82
81
8
85
84

8
C
81
82
85
83
84a
84

Fig. 11
Fig. 12
Fig. 13
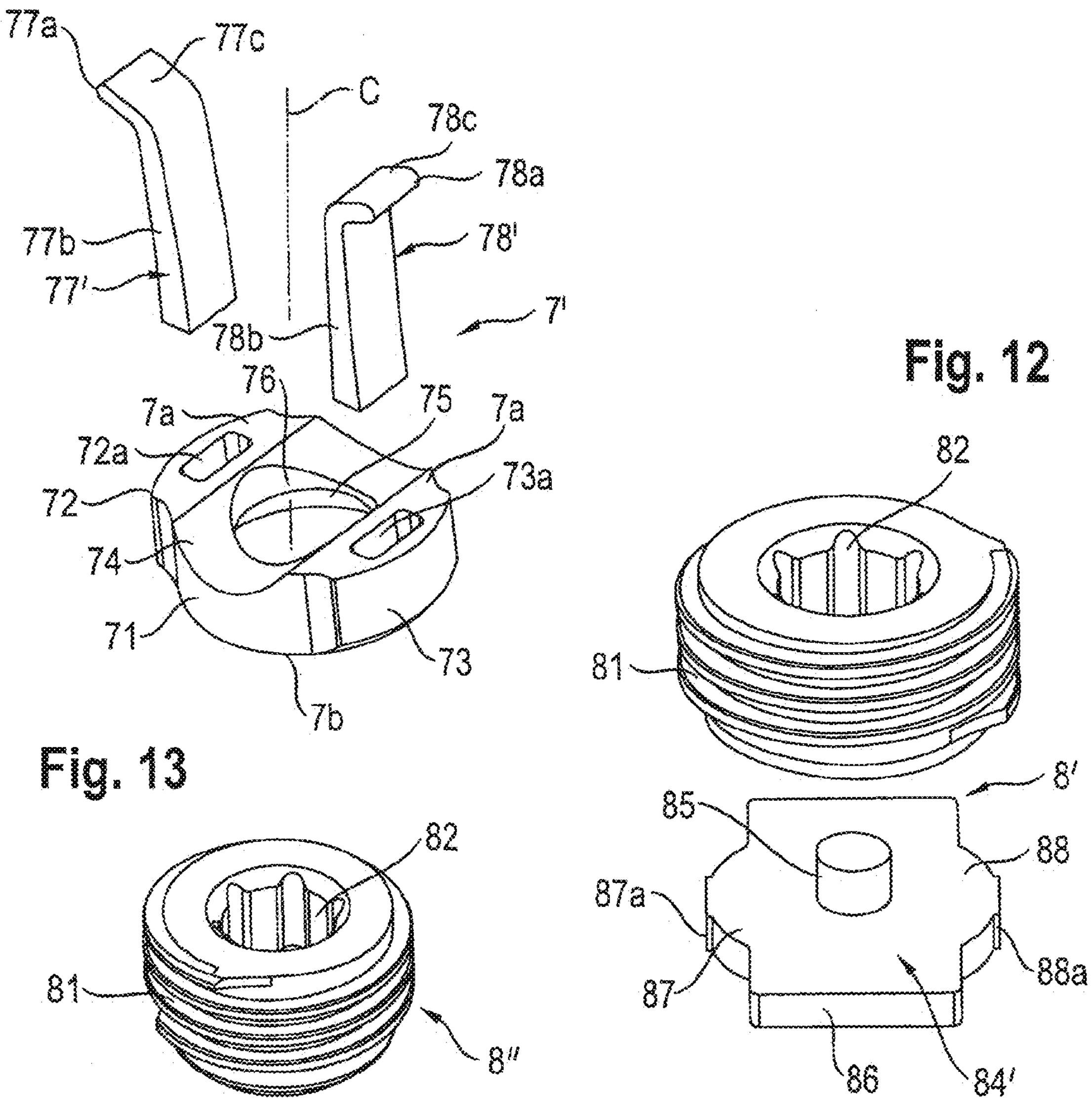
Fig. 14
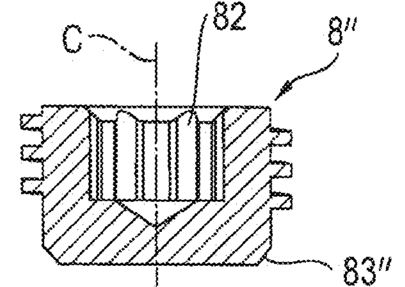

C
100
8''
59a
78a
56a
78''
7''
5'
6
1
3
52
58a
77a
55a
77''
51a
78c''
78b''
83''
77c''
77b''

POLYAXIAL BONE ANCHORING DEVICE

CROSS-REFERENCE TO RELATED APPLICATIONS

This application is a continuation of U.S. patent application Ser. No. 18/093,271, filed Jan. 4, 2023, which is a continuation of U.S. patent application Ser. No. 16/950,723, filed Nov. 17, 2020, now U.S. Pat. No. 11,576,708, which is a continuation of U.S. patent application Ser. No. 16/194,995, filed Nov. 19, 2018, now U.S. Pat. No. 10,864,030, which is a continuation of U.S. patent application Ser. No. 14/822,583, filed Aug. 10, 2015, now U.S. Pat. No. 10,159,519, which claims the benefit of U.S. Provisional Application Ser. No. 62/035,666, filed on Aug. 11, 2014, the contents of which are hereby incorporated by reference in their entirety, and claims priority from European Patent Application EP 14180588.7, filed on Aug. 11, 2014, the contents of which are hereby incorporated by reference in their entirety.

BACKGROUND

The invention relates to a polyaxial bone anchoring device, in particular for use in spinal or trauma surgery. The polyaxial bone anchoring device comprises a bone anchoring element with a shank to be anchored to a bone and a head. The head is pivotably held in a receiving part and can be locked at an angle relative to the receiving part by applying pressure onto it via a pressure member. With the receiving part, the bone anchoring element can be coupled to a stabilization rod that can be secured by a locking member. The pressure member comprises a deformable portion. First, the locking member applies a load to the pressure member that deforms the deformable portion whereby the head is locked. Thereafter the locking member comes into contact with the rod and locks the rod. The polyaxial bone anchoring device permits locking the head and the rod in a sequential manner, using a tool with a single drive portion that engages the locking member.

U.S. Pat. No. 8,088,152 B1 describes an orthopedic retaining system comprising at least one bone screw which has a head part and a shaft pivotably mounted thereon. A clamping sleeve is mounted in the head part, which can be pressed against the threaded shaft from its upper side to secure the threaded shaft relative to the head part. Further, a clamping device is provided by means of which the clamping sleeve and a retaining bar are pressed into the head part. The clamping device comprises an elastically deformable pressure member which is displaced into a clamping position during actuation of the clamping device.

US 2012/0253408 A1 describes a bushing for a bone screw assembly that includes a distal portion, a receiver portion, and a proximal portion. The distal portion includes a distal engagement surface that engages with a head of a bone screw. The receiver portion receives a fixation rod. The proximal portion includes a proximal engagement surface that engages with a locking member and a deformable portion that deforms from a first configuration to a second configuration based on a force applied by the locking member.

US 2013/0345761 A1 describes a polyaxial bone anchoring device comprising a bone anchoring element with a shank and a head and a receiving part pivotably coupled to the shank and having a channel for receiving a rod. A pressure member is arranged in a receiving part and is configured to exert pressure onto the head to lock the head in a receiving part. The pressure member has a deformable portion. Load applied to the pressure member by a locking member clamps the head and thereafter contacts the pressure member such that the deformable portion is deformed and the locking member comes into contact with the rod and clamps the rod.

While known devices allow locking of the head of a bone anchoring device in the receiving part first and thereafter locking of the rod with a single instrument in a sequential manner, the necessary locking force for locking the devices is high. This results from the fact that the final step of clamping and locking the rod involves both the deformation of a deformable portion of the pressure member as well as a force applied for clamping and locking the rod. The force necessary for the deformation is lost for the clamping. Therefore, a relatively high force has to be applied to safely lock the rod.

SUMMARY

It is an object of the invention to provide a polyaxial bone anchoring device that allows for a sequential locking of the head and the rod to the receiving part with an instrument having a single drive portion and that requires a reduced force for locking. In addition, it is an object of the invention to provide a system of such a polyaxial bone anchoring device and at least two rods having different diameters where the bone anchoring device is configured to receive any of the rods and that provides a sequential locking function requiring a reduced force for locking.

The polyaxial bone anchoring device comprises a pressure member having a pressure exerting surface that exerts pressure onto the head and a deformable portion with a free end that is supported in the receiving part. In combination with a locking member, a force is exerted onto the deformable portion of the pressure member that deforms the deformable portion from a first configuration to a second configuration where the pressure exerted by the pressure member onto the head increases. Such a configuration allows for the deformable portion to function similar to a toggle lever that adjusts from an angled configuration when not clamped into a more substantially straight configuration when clamped. For locking the rod, the locking member is further advanced and tightened without a further deformation of the deformable portion of the pressure member. Therefore, a loss of force during locking of the rod due to deformation of the pressure member is reduced. This permits higher clamping forces acting onto the rod, and in turn, increases the safety of the locking.

In one embodiment, the deformable portion of the pressure member is elastically deformable and comprises a highly elastic material, in particular a material with superelastic properties, such as a nickel-titanium (NiTi)-alloy, in particular Nitinol, or, for example, Beta-titanium. In this embodiment, due to the high elasticity of the deformable portion, a loss of force during deformation can be further reduced.

In one embodiment, the pressure member can be a monolithic piece made of such a highly elastic material. In another embodiment, only the deformable portion of the pressure member is made from the highly elastic material and is attached to another portion of the pressure member that may be manufactured from different material. This can reduce the manufacturing costs and facilitate easier manufacturing. Due to the elasticity of the deformable portion, size tolerances of the pressure member and the parts interacting therewith can be balanced.

In a still further embodiment, the locking of the head is maintained by the pressure exerted by the pressure member in the second configuration, even if the locking member is loosened. Hence, further adjustments of the rod position are possible while the head still remains in the locked angular position relative to the receiving part. The deformable portion can be adjusted back to the first configuration, for example, by applying an instrument.

The polyaxial bone anchoring device according to the embodiments of the invention allows for a sequential locking, where first the head is locked and thereafter the rod is fixed by the application of a single instrument with a single drive portion. This facilitates easier handling of the polyaxial bone anchoring device during surgery.

In a still further embodiment, the pressure member is positioned in the receiver in the first configuration in such a manner that the pressure member exerts pressure onto the head to maintain the head by friction in a desired angular orientation before locking. This further facilitates adjustment of the orientation of the receiving part relative to the bone anchoring element before inserting the rod.

The polyaxial bone anchoring device may be of a top loading type, where the bone anchoring element is inserted into the receiving part from a top side, i.e. the side from which the locking member is inserted. Alternatively, the bone anchoring device may be of a bottom loading type, where the head of the bone anchoring element is inserted into the receiving part from a bottom side, i.e. from the side opposite to where the locking member is inserted.

In a still further embodiment, a support surface of the pressure member for supporting the rod is configured to support rods having different diameters. This allows use of the sequential locking mechanism with different rods using one single polyaxial bone anchoring device, regardless of the size of the rod.

BRIEF DESCRIPTION OF THE DRAWINGS

Further features and advantages of the invention will become apparent from the description of embodiments by means of the accompanying drawings. In the drawings:

FIG. 3 shows a perspective view from a top of a receiving part of the polyaxial bone anchoring device according to the first embodiment.

FIG. 4 shows a perspective view from a bottom of the receiving part of the polyaxial bone anchoring device according to the first embodiment.

FIG. 5 shows a top view of the receiving part of FIGS. 3 and 4.

FIG. 6 shows a cross-sectional view of the receiving part of FIGS. 3 to 5, the cross-section taken along line A-A in FIG. 5.

FIG. 11 shows a perspective exploded view of a modified pressure member of the polyaxial bone anchoring device according to the first embodiment.

FIG. 12 shows a perspective exploded view of a further modification of a two-part locking member.

FIG. 13 shows a perspective view of a modified locking member of the polyaxial bone anchoring device according to the first embodiment.

FIG. 14 shows a cross-sectional view of the locking member of FIG. 13.

DETAILED DESCRIPTION

Figures 1, 2:
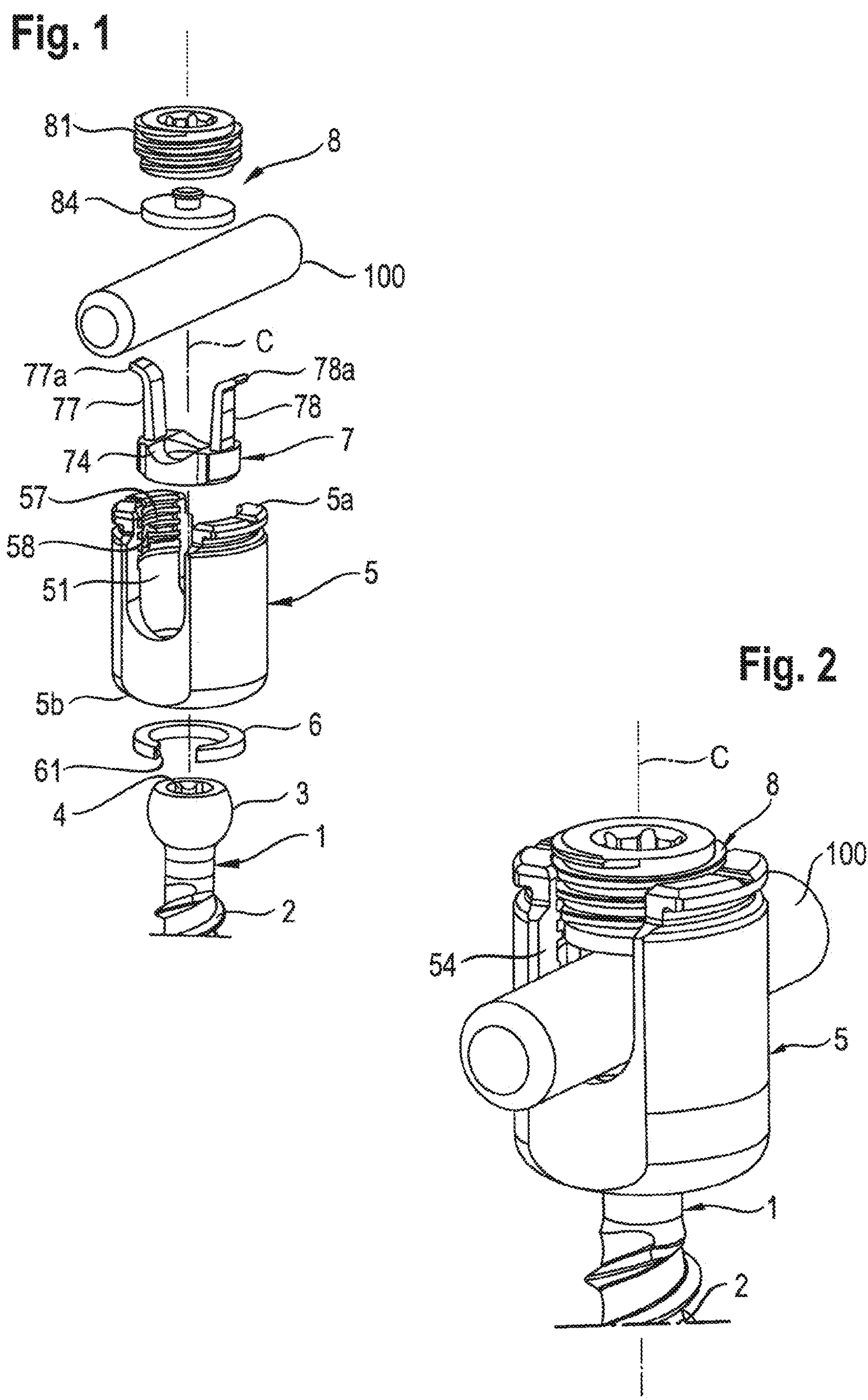
FIG. 1 shows a perspective exploded view of a polyaxial bone anchoring device according to a first embodiment.
FIG. 2 shows a perspective view of the polyaxial bone anchoring device according to the first embodiment in an assembled state.

A polyaxial bone anchoring device according to a first embodiment is shown in FIGS. 1 and 2. The polyaxial bone anchoring device comprises an anchoring element 1 having a shank 2 with a threaded portion and a head 3. The head 3 has a spherically-shaped outer surface portion and, on its side opposite to the shank 2, a recess 4 for engagement with a tool. A receiving part 5 is provided for coupling the bone anchoring element 1 to a rod 100. The polyaxial bone anchoring device in FIGS. 1 and 2 is of the bottom loading type, i.e. the bone anchoring element 1 is inserted into the receiving part 5 from a bottom end of the receiving part 5. To retain the head 3 in the receiving part, a retainer element 6 is provided. In addition, a pressure member 7 is arranged in the receiving part to exert pressure onto the head 3 of the bone anchoring element 1. For locking the head 3 and the rod 100 relative to the receiving part 5, a locking member 8 is provided that is insertable into the receiving part 5.

Referring further to FIGS. 1 to 6, the receiving part 5 has a first end or top end 5*a*, a second end or bottom end 5*b*, and has a substantially cylindrical construction, with a longitudinal axis C that goes through the top end 5*a* and the bottom end 5*b*. Coaxial with the longitudinal axis C, a first coaxial bore 51 is provided extending from the top end 5*a* to a predetermined distance from the bottom end 5*b*. A second coaxial bore 52 with a smaller diameter than that of the first bore 51 extends from the bottom end 5*b* into the first bore 51 and serves as an accommodation space for the head 3. The second bore 52 leads into a bottom opening 52*a* with an inner diameter greater than the outer diameter of the head 3 at the bottom end 5*b*. This permits insertion of the head 3 through the opening 52*a* from the bottom end 5*b*. Furthermore, at a distance from the second end 5*b*, an annular groove 53 is provided for accommodating the retainer element 6. An axial length of the second bore 52 is such that when the head 3 is retained by the retainer element 6, an uppermost portion of the head 3 protrudes into the first bore 51 and is configured to be engaged by the pressure member 7. It shall be noted that the diameter of the first bore 51 does not need to be larger than the diameter of the second bore 52.

The receiving part 5 further comprises a U-shaped recess 54 starting at the top end 5*a* and extending in the direction of the bottom end 5*b*. By means of the U-shaped recess 54, two free legs 55, 56 are formed that define a channel for receiving the rod 100. Adjacent to the top end 5*a*, an internal thread 57 is provided at the inner surface of the legs 55, 56. In the embodiment shown, the internal thread 57 is a flat thread having substantially horizontal upper and lower thread flanks. Any other thread form can be used for the internal thread 57. A thread form that reduces or eliminates splaying of the legs 55, 56, however, is preferable.

As depicted in particular in FIGS. 3 and 6, two recesses 58, 59 are formed at an inner wall of the legs 55, 56, respectively, that have the purpose of accommodating a portion of the pressure member 7 therein. The recesses 58, 59 are located at substantially the center of each leg 55, 56 in the circumferential direction and at a lower portion of the thread 57 in the axial direction. An upper wall 58*a*, 59*a* or an upper corner of the recesses 58, 59 forms a support for the pressure member 7 as explained below.

As can be seen in FIGS. 1, 7 and 10*a* to 10*f*, the pressure member 7 has a substantially cylinder-segment shaped central portion 71 and two side flanges 72, 73 provided on opposite sides of the central portion 71 and also having cylindrical outer surface portions. At a top surface 7*a* of the pressure member 7 between the flanges 72, 73, a rod supporting surface 74 is provided in the form of a substantially cylinder segment-shaped recess with a cylinder axis being perpendicular to a central axis C that is configured to coincide with the central axis C of the receiving part 5. The radius of the cylinder segment-shaped rod supporting surface 74 can match the radius of a rod 100 to be supported thereon. The pressure member 7 further comprises a substantially spherical recess 75 opposite to the upper surface 7*a* with a radius of the sphere matching the radius of the spherical head 3. The inner surface of the recess 75 forms a pressure-exerting surface. A lower edge of the recess 75 forms a bottom end 7*b* of the pressure member 7. In addition, a coaxial through-hole 76 extends through the central portion 71 to allow access with a driver or another instrument to the head 3.

Figures 7, 8, 9:
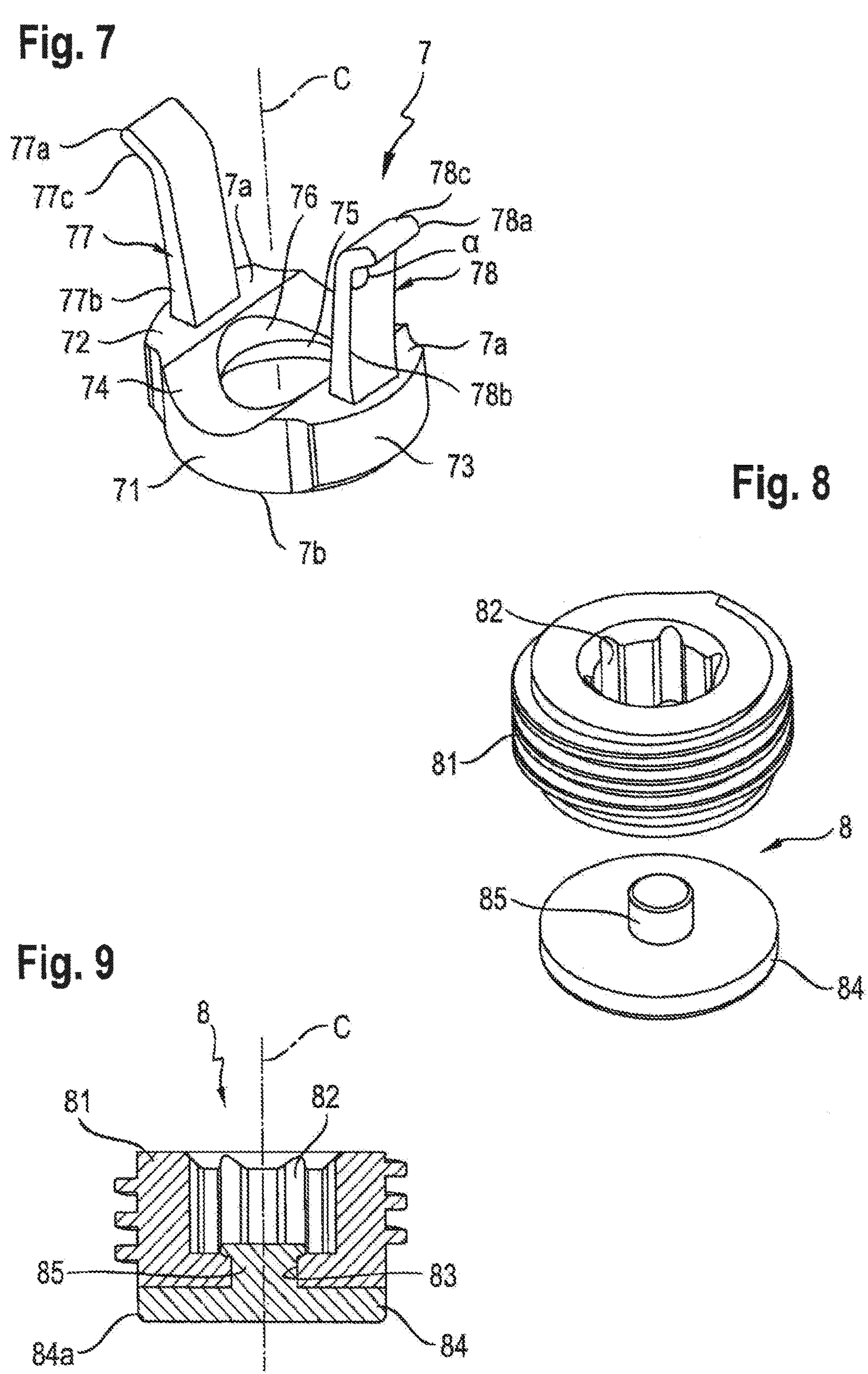
FIG. 7 shows a perspective view of a pressure member of the polyaxial bone anchoring device according to the first embodiment.
FIG. 8 shows a perspective exploded view of a locking member of the polyaxial bone anchoring device according to the first embodiment.
FIG. 9 shows a cross-sectional view of the locking member of FIG. 8, the cross-section taken in a plane containing a central axis of rotation of the locking member.

As shown in FIG. 7, two upstanding arms 77, 78 protrude from the upper surface 7*a* of the pressure member 7. The arms 77, 78 are respectively positioned substantially at the middle of the upper surface 7*a* of the flanges 72, 73 and each arm 77, 78 has a substantially rectangular cross-section. In the embodiment shown, a long side of the rectangle is substantially parallel to the cylinder axis of the rod supporting surface 74 and is smaller than a width of the flanges 72, 73 in this same direction. A width of each of the arms 77, 78 in a direction perpendicular to the cylinder axis of the rod supporting surface 74 is also smaller than the width of the flanges 72, 73 in this same direction, so that the arms 77, 78 are spaced apart from the edges of the flanges 72, 73. In addition, the thickness of the arms 77, 78 decreases in an upward direction.

As further shown in FIG. 7, each arm 77, 78 comprises a free end 77*a*, 78*a*. Adjacent to the upper surface 7*a* of the pressure member 7, each of the arms 77, 78 has a substantially vertically extending long portion 77*b*, 78*b*. From the end of the long portions 77*b*, 78*b*, short portions 77*c*, 78*c* extend radially outward and away from the long portions 77*b*, 78*b* at an angle α of substantially 90° or greater. The long portions 77*b*, 78*b* may be twice as long as the short portions 77*c*, 78*c* or longer. The length of the arms is such that the long portions 77*b*, 78*b* extend above an upper surface of a rod that is placed onto the rod support surface 74.

In this embodiment, the pressure member 7 is a monolithic piece. It may be formed entirely from a highly elastic material. Such a material can be, for example, a metal or a metal alloy having superelastic properties. Such metal alloy can be, for example, a nickel-titanium alloy (NiTi alloy), such as Nitinol, or Beta-titanium. However, other materials that can provide the necessary high elasticity can also be used.

Due to the shape and the material, the arms 77, 78 are flexible. In particular, in a first configuration, the arms 77, 78 are in their resting position that is defined by the bent shape as shown in FIG. 7, wherein the short portions 77*c*, 78*c* form an obtuse angle α with the long portions 77*b*, 78*b*. In a second configuration, the arms 77, 78 are deformed such that the angle α between the short portions 77*c*, 78*c* and the long portions 77*b*, 78*b* is increased, and the long portions may be deflected outward. In the second configuration, a load can be transferred through the arms 77, 78 onto the head 3. In other words, the pressure member 7 can behave similar to toggle levers formed by the arms 77, 78, that act between the receiving part 5 and the head 3, where a bending area of the arms 77, 78 corresponds to a middle point of rotation or, for example, a pivot point of a toggle level.

As can be seen in particular in FIGS. 10*a* to 10*f*, when the pressure member 7 is inserted into the receiving part 5 and the free ends 77*a*, 78*a* of the arms 77, 78 abut against the support surfaces 58*a*, 59*a* in the recesses 58, 59, the pressure member is accommodated in the first bore 51 such that a gap exists between the lower edge 7*b* of the pressure member 7 and the bottom of the first bore 51.

As depicted in FIG. 1 and FIGS. 10*a* to 10*f*, the retaining element 6 is formed as a slotted ring having a slot 61 that renders the retainer element 6 radially compressible and expandable. The outer size of the retainer element 6 is such that the retainer element 6 can be inserted into the groove 53 in a slightly compressed manner, and is held in the groove 53 under a pre-load.

Referring now in particular to FIGS. 1 and 2 as well as FIGS. 8 to 10*f*, the locking member 8 is a two-part locking member that includes a set screw 81 and a washer 84 rotatably connected to the set screw 81. The set screw 81 is configured to engage the internal thread 57 of the legs 55, 56 and has an engagement portion 82 for a driver on its upper side. A through-hole 83 may be provided on the lower side of the set screw 81. The washer 84 may be connected to the set screw 81 with a central coaxial pin 85 that extends through the through-hole 83 and is deformed on the other side of the through hole 83 to provide a rivet-like connection. A lower edge 84*a* of the washer 84 is rounded. This ensures a smooth sliding contact between the locking member 8 and the pressure member 7. The washer 84 may have a same outer contour as a portion of the set screw 81.

The receiving part 5, the retainer element 6, the bone anchoring element 1 and the locking member 8 can each be made of a material that is different from the material of the pressure member 7. In particular, the materials used can be any body-compatible material such as a body-compatible metal or metal alloy, such as stainless steel, titanium or a body-compatible plastic, such as polyetheretherketone (PEEK). The parts can all be made of the same or of different materials. In a still further embodiment, all parts of the polyaxial bone anchoring device can be made of the same material as the pressure member 7.

The bone anchoring device may be preassembled as follows. In a first method of assembly, the head 3 of the bone anchoring element 1 is inserted in the receiving part 5 through the lower opening 52*a*. Then, the retaining element 6 is compressed and inserted into the groove 53 from the lower opening 52*a*. Once the retaining element 6 is in the groove 53, the head 3 is pivotably held by the retaining element 6 and cannot be removed through the lower opening 52*a*. In an alternative method of assembly, the retaining element 6 is placed into the groove 53 and the bone anchoring element 1 is then inserted through the top end 5*a* of the receiving part 5, such that the shank 2 extends through the lower opening 52*a* and the head 3 rests on the retaining element 6. The retaining element 6 prevents the head 3 from being pulled through the lower opening 52*a* of the receiving part 5.

The pressure member 7 is inserted through the top end 5*a* in an orientation in which the cylinder axis of the rod supporting surface 74 is aligned with the longitudinal axis of the U-shaped recess 54 of the receiving part. The arms 77, 78 of the pressure member 7 are slightly compressed towards each other during insertion, such that the free ends 77*a*, 78*a* of the arms 77, 78 snap into the recesses 58, 59 of the receiving part 5 and are supported by the upper wall 58*a*, 59*a* of the recesses 58, 59, respectively, as depicted in FIGS. 10*a* to 10*f*. The pressure exerting surface 75 of the pressure member 7 at least partially contacts the outer surface of the head 3. The dimensions of the pressure member 7 may be such that, in the assembled state when the head 3 is not yet locked relative to the receiving part 5, the pressure member 7 exerts a pre-stress onto the head 3 that maintains the bone anchoring element 1 in the receiving part 5 at a desired angular orientation relative to the receiving part 5 before locking by means of friction between the pressure exerting surface 75 and the head 3.

Figures 10A, 10B, 10C:
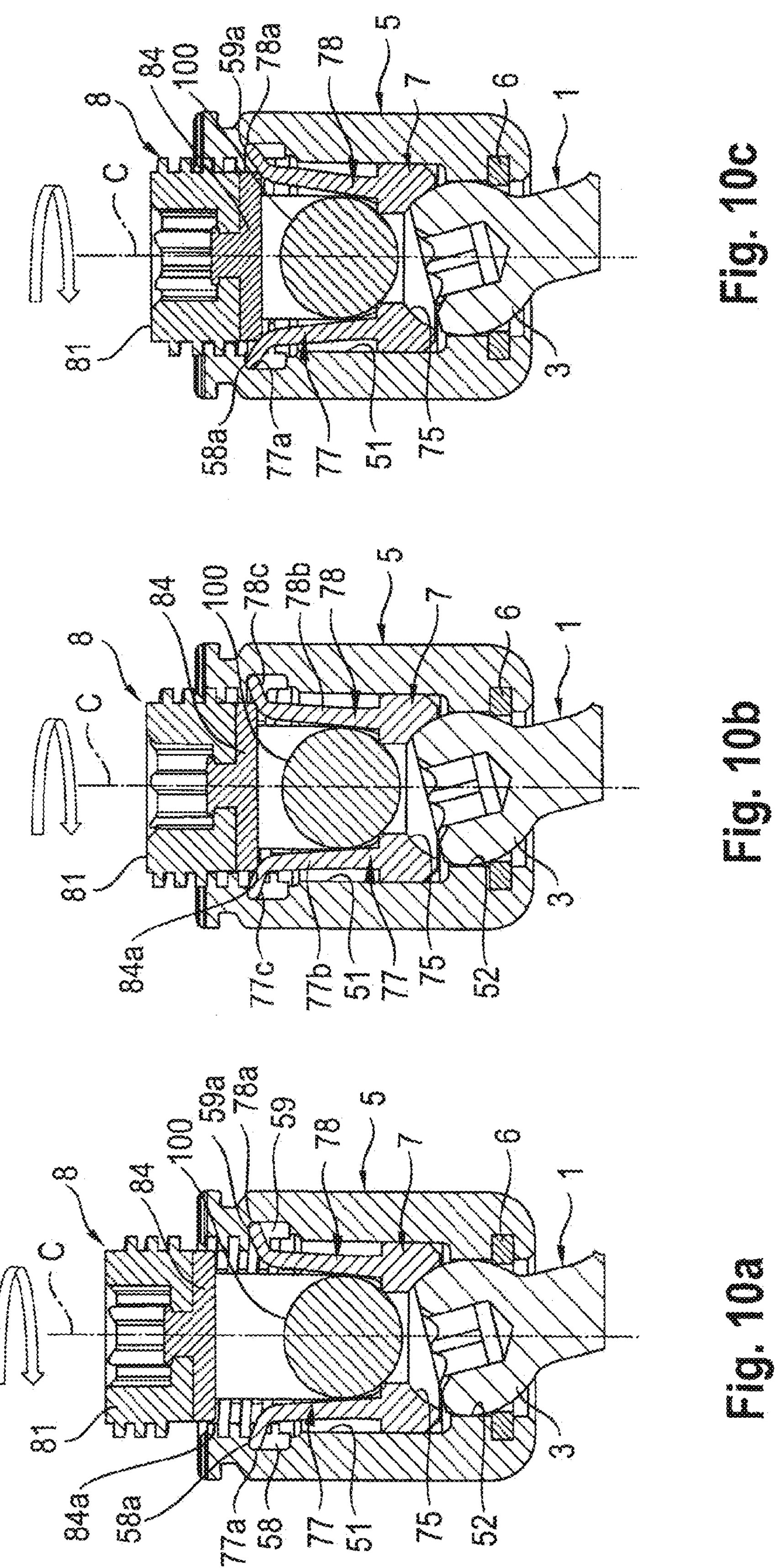
FIGS. 10*a* to 10*f* show respective cross-sectional views of the polyaxial bone anchoring device according to the first embodiment that illustrate the steps of inserting and advancing the locking member into the receiving part for locking the head and the rod in a sequential manner.

As illustrated in FIGS. 10*a* to 10*c*, at least a central portion of the arms 77, 78 is spaced apart from the inner wall of the first bore 51, such that there is a gap between the inner wall of the first bore 51 and an outer surface of the arms 77, 78 that allows the arms 77, 78 to be deflected outward.

The use and function of the polyaxial bone anchoring device will be explained referring to FIGS. 10*a* to 10*f*. Usually, at least two bone anchoring elements 1 are inserted into bone parts or adjacent vertebrae and the U-shaped recesses 54 of the corresponding receiving parts 5 are aligned to receive the rod 100. As depicted in FIG. 10*a*, the locking member 8 is screwed in between the legs 55, 56. When the locking member 8 is further screwed in, the lower rounded edge 84*a* of the washer 84 contacts the short portions 77*c*, 78*c* of the arms 77, 78 near the transition to the long portions 77*b*, 78*b* (FIG. 10*b*). Because the washer 84 is rotatably connected to the set screw 81, the washer 84 basically does not rotate when the set screw 81 is further advanced into the receiving part 5. This results in the forces exerted by the locking member 8 onto the arms 77, 78 being substantially axial, where radial forces and transverse forces are reduced.

Figures 10D, 10E, 10F:
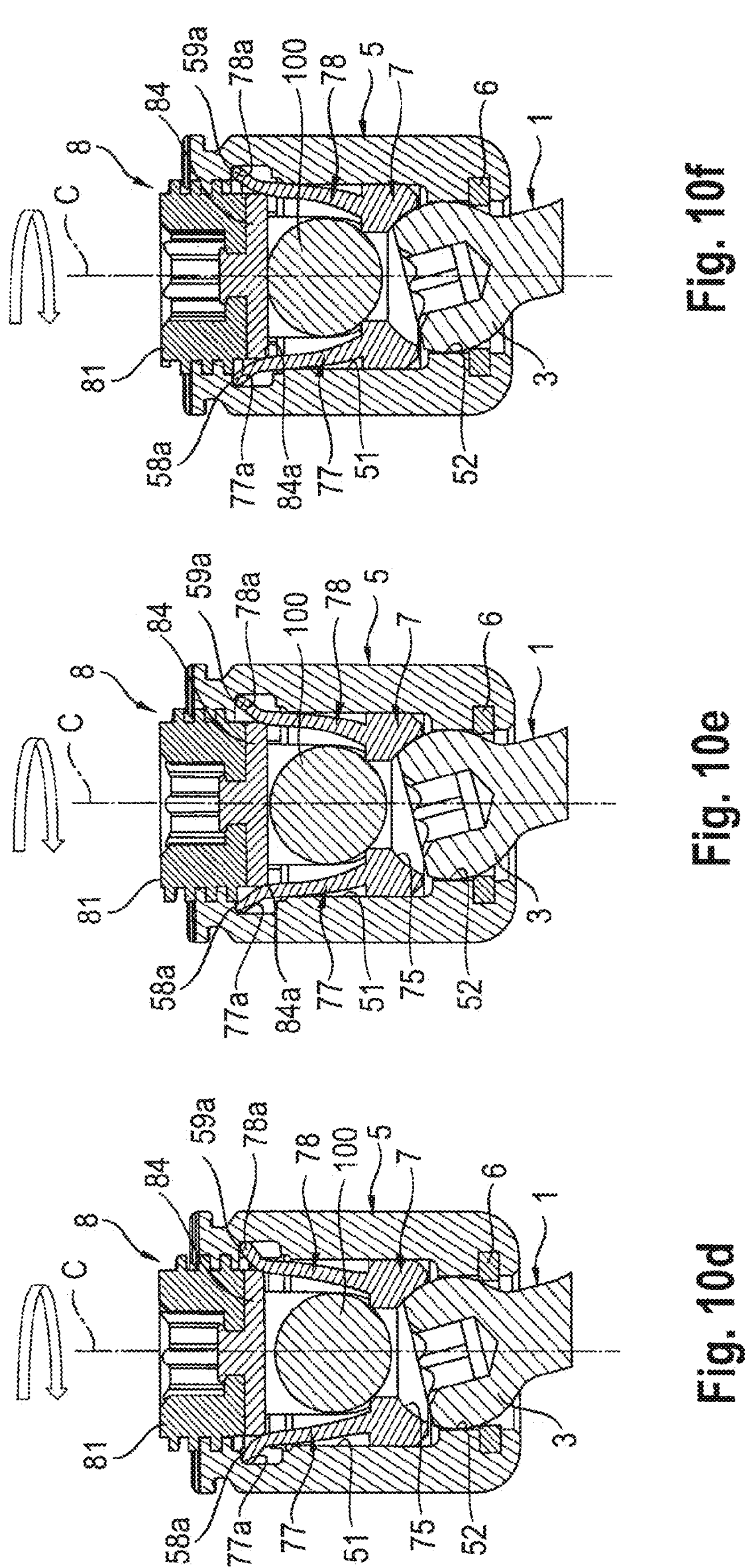

The locking member 8 exerts a force onto the arms 77, 78 that deforms the arms 77, 78 as can be seen in FIGS. 10*c* and 10*d*. Thereby, the arms 77, 78 of the pressure member 7 tend to become more straightened as the locking member 8 is advanced in the receiving part 5. Because the free ends 77*a*, 78*a* of the arms 77, 78 are supported in the receiving part 5 and the pressure exerting surface 75 is supported on the head 3, which itself is supported on the retaining element 6, there is limited or no space for the arms 77, 78 to extend in the axial direction, so the long portions 77*b*, 78*b* of the arms 77, 78 are deflected radially outward as depicted in FIGS. 10*c* to 10*e*. The deformation of the arms 77, 78 results in a continuously increasing pressure on the head 3.

As illustrated in FIG. 10*f*, the long portions 77*b*, 78*b* of the arms 77, 78 are further deformed outward during tightening of the locking member 8 and extend into the space provided by the first bore 51. When the arms 77, 78 are in the second configuration as shown in FIG. 10*e*, the head 3 is fully locked by the pressure exerted onto it by the pressure member 7. The second configuration is maintained even if the locking element 8 is advanced further downward and thereby slides along the inner side of the arms 77, 78, so that the advancement of the locking element 8 may require only little force. In the second configuration prior to locking the rod 100, the rod 100 is still movable because the locking member 8 is not in contact with the rod 100.

Finally, as depicted in FIG. 10*f*, further tightening of the locking member 8 advances the locking member 8 towards the rod surface, until the rod 100 is fixed by the pressure exerted onto it by the locking member 8.

In the first embodiment, a loosening of the locking member 8 causes the arms 77, 78 to return to the first configuration due to the high elasticity of the arms 77, 78. After loosening the locking member 8, the positions of the head 3 and the rod 100 relative to the receiving part 5 can be adjusted again.

FIG. 11 shows a modification of the pressure member. All portions that are identical or similar to the portions of the pressure member 7 of the first embodiment are marked with the same reference numerals, and the descriptions thereof will not be repeated. The pressure member 7' has arms 77', 78' that are separate pieces from the main part 71 and that are insertable into recesses 72*a*, 73*a* in the upper surface 7*a* of the flanges 72, 73. The separate arms 77', 78' are connected to the pressure member 7, for example, by a press-fit connection or any other connection that prevents inadvertent disassembly. In the pressure member 7', only the arms 77', 78' are made from a highly elastic material, such as a material exhibiting superelastic properties like a nickel-titanium (NiTi) alloy, for example Nitinol or, for example, Beta-titanium. The main part 71 and the flanges 72, 73 can be made from another material, such as stainless steel or titanium or any other body compatible material. With this embodiment, the manufacturing of the pressure member 7' can be more easily facilitated and costs can be saved.

FIG. 12 shows a perspective exploded view of a modified locking member. The locking member 8' is a two-part locking member that comprises the set screw 81 and a washer 84' that can be rotatably connected to the set screw 81, for example, by a rivet-like connection. The washer 84' has a substantially rectangular main portion 86 and two opposite cylinder-segment shaped flanges 87, 88 that extend from the main portion 86 on opposite sides. The flanges 87, 88 each have substantially vertically extending and substantially flat outermost surface portions 87*a*, 88*a*, with a width that is substantially the same or greater than the widths of the arms 77, 78 of the pressure member 7. Such a configuration allows for the washer 84' to more smoothly slide along the inner surface of the arms 77, 78 of the pressure member 7 that faces towards the central axis C when the locking member 8' is advanced in the receiving part 5. The substantially flat vertical surface portions 87*a*, 88*a* allow for a better transfer of the pressure force applied by the washer 84' onto the arms 77, 78. The rectangular main portion 86, for example, extends into the U-shaped recess 54 of the receiving part 5 and prevents the washer 84' from rotating when the set screw 81 is screwed in. Therefore, the occurrence of transverse forces acting onto the arms 77, 78 can be decreased or avoided.

In a further modification depicted in FIGS. 13 and 14, the locking member 8" is monolithic. The locking member 8" is formed as a set screw with an engagement portion 82 and a beveled lower edge 83" opposite to the engagement portion 82. The beveled lower edge 83" ensures that sufficient pressure is exerted onto the arms 77, 78 when the locking member 8" is moved downward in the bore 51.

A second embodiment of the polyaxial bone anchoring device will be described with reference to FIGS. 15*a* to 15*d*. The second embodiment of the polyaxial bone anchoring device differs from the first embodiment in the design of the receiving part and the pressure member. The locking member used in this embodiment is the single part locking member 8" as described before. However, the two-part locking members as described before can also be used.

The receiving part 5' comprises an enlarged bore section 51*a* that is provided approximately in the middle of the receiving part 5' in an axial direction. The enlarged bore section 51*a* serves to provide more space for deforming the arms 77", 78" of the pressure member 7". In addition, two transverse through bores 55*a*, 56*a* are respectively positioned in a transverse direction at substantially the centers of the legs 55, 56. The through bores 55*a*, 56*a* are configured to permit access to the first bore 51 with an instrument.

Figures 15A, 15B, 15C, 15D:
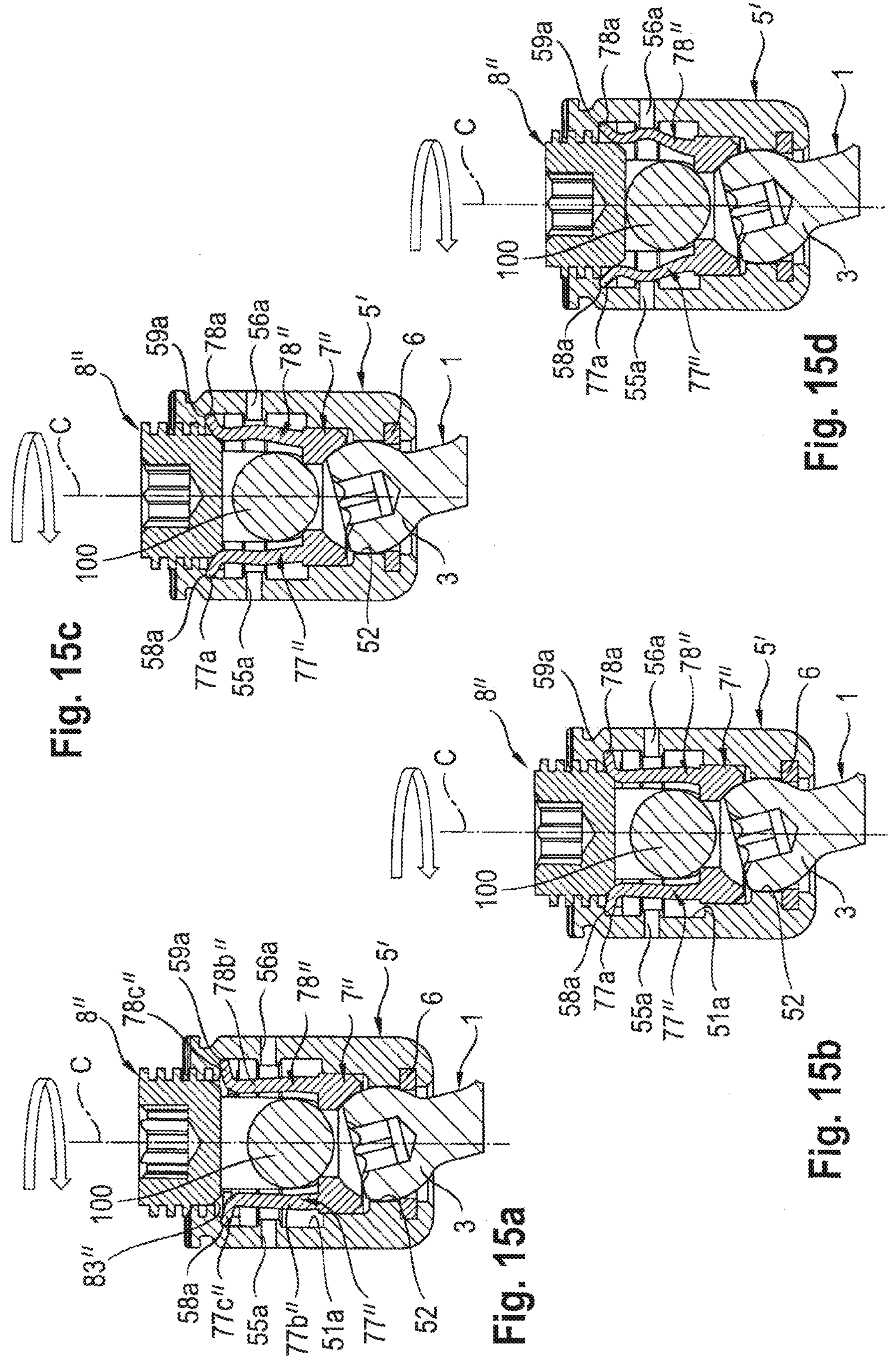
FIGS. 15*a* to 15*d* show cross-sectional views, respectively, of a polyaxial bone anchoring device according to a second embodiment, illustrating steps of inserting and advancing the locking member to lock the head and the rod in a sequential manner.

As depicted in particular in FIG. 15*a*, the pressure member 7" differs from the previously discussed pressure members with respect of the shape of the arms 77", 78". The arms 77", 78" have long portions 77*b*", 78*b*" that are slightly bent outward near the upper surface 7*a* of the main body of the pressure member 7". Furthermore, the short portions 77*c*", 78*c*" each form an angle of 90° or only slightly larger than 90° with the respective long portions 77*b*", 78*b*". The bending properties of the arms 77", 78" are different from the arms 77, 78 of the first embodiment. When pressure is exerted onto the short portions 77*c*", 78*c*" near the bending area (i.e., the area between the short portions 77*c*", 78*c*" and the long portions 77*b*", 78*b*"), the pressure exerted onto the arms 77*c*", 78*c*" deforms the vertical long portions 77*b*", 78*b*" outward so that the arms 77", 78" assume an approximate S-shape (FIG. 15*d*).

As illustrated in FIGS. 15*a* and 15*b*, the locking member 8" can be screwed into the receiving part 5' until the beveled edge 83" abuts against the arms 77", 78" in the region of the bending area (FIG. 15*b*). Further advancement of the locking member 8" results in an outward bending of the long portion 77*b*", 78*b*" of the arms 77", 78" (FIG. 15*c*). In this configuration, the pressure exerted onto the head 3 is increased. Further screwing in of the locking member 8" results in a deformation of the arms 77", 78" to an approximate S-shape, whereby the long portions 77*b*", 78*b*" snap outward, for example, like a flip-flop. In this configuration, the head 3 is locked. The locking member 8" can be further advanced until it presses onto the upper surface of the rod 100, resulting in a locking of the rod 100 (FIG. 15*d*).

In the configuration shown in FIG. 15*d*, the deformation of the arms 77", 78" remains permanent, unless the arms 77", 78" are deformed back to their original shapes. Hence, the locking member 8" can be unscrewed in order to readjust the position of the rod 100 relative to the receiving part 5', while the angular position of the head 3 relative to the receiving part 5' remains locked. In this embodiment, the locked head 3 can be unlocked by applying an instrument that extends through the through bores 55*a*, 56*a* and pushes the arms 77", 78" back into their original positions.

Figure 16:
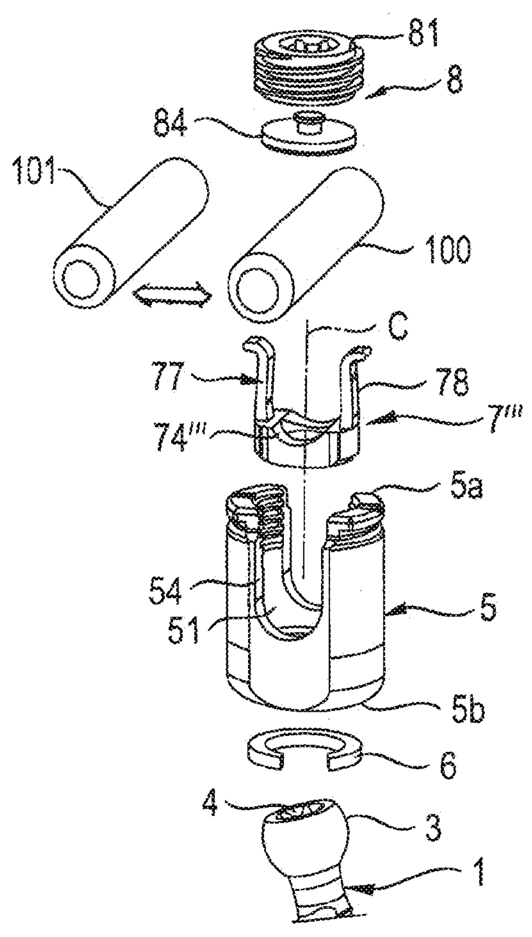
FIG. 16 shows a perspective exploded view of a system including a polyaxial bone anchoring device and two rods having different diameters.
Figure 17A:
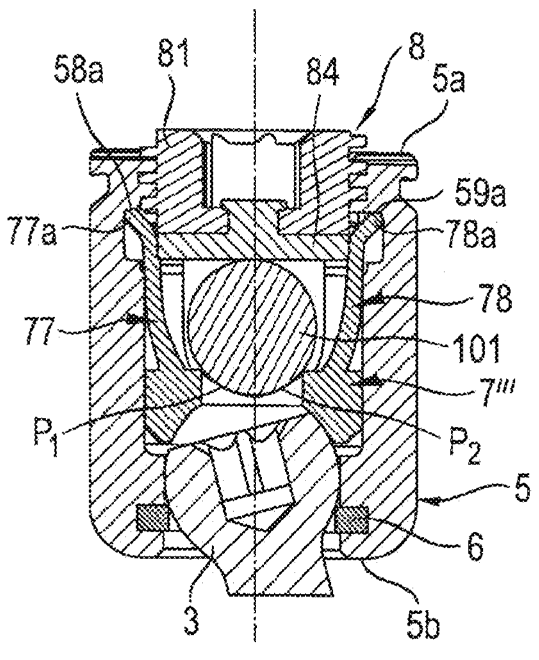
FIG. 17*a* and FIG. 17*b* show cross-sectional views of the polyaxial bone anchoring device of FIG. 16, with the inserted rods having different diameters, respectively.
Figure 17B:
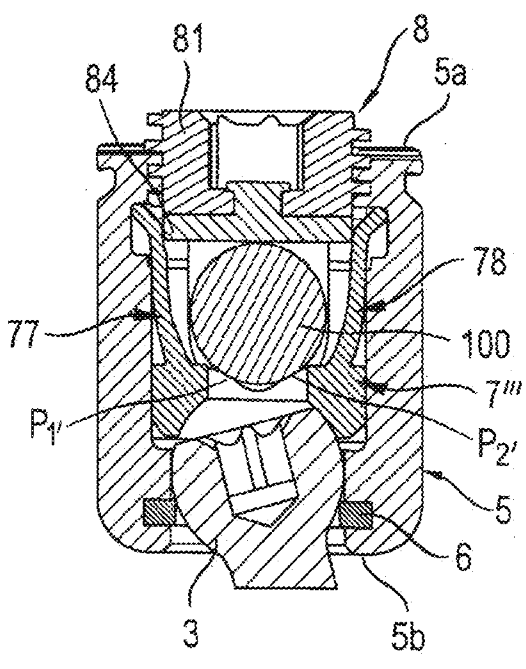

Referring to FIG. 16, a third embodiment of the polyaxial bone anchoring device is shown. Parts and portions that are identical or similar to the previous embodiments have the same reference numerals, and the descriptions thereof will be not repeated. In this embodiment, the pressure member 7'" comprises a rod supporting surface 74'" that has a substantially v-shaped cross-section in a plane perpendicular to a longitudinal axis of the rod supporting surface 74'". As shown in FIG. 16, such a configuration facilitates using rods 100, 101 that have different diameters with the polyaxial bone anchoring device. As depicted in FIG. 17*a*, a rod 101 with a smaller diameter compared to the rod 100 is supported on the rod supporting surface 74'" of the pressure member 7'". The rod 101 is supported along opposite lines of contact P1, P2 that extend along the length of the rod supporting surface 74'". The arms 77, 78 of the pressure member 7'" extend above the surface of the inserted rod 101. As in the previous embodiments, the locking member 8 can be screwed in to first lock the head 3 relative to the receiving part 5' and thereafter lock the rod 101 relative to the receiving part 5'. As shown in FIG. 17*b*, the rod 100 with a diameter greater than that of the rod 101 can be supported at substantially two contact lines P1', P2' that may be positioned higher from the bottom of the rod supporting surface 74'" than the position of the contact lines P1, P2 when the rod 101 is used. When the rod 100 is used, the arms 77, 78 can also extend above the surface of the rod 100. Advancing the locking member 8 into the receiving part 5 first locks the head 3 relative to the receiving part 5 and thereafter locks the rod 100 relative to the receiving part 5.

In this embodiment, a system including the polyaxial bone anchoring device and at least two rods having different diameters where the bone anchoring device is configured to receive any of the rods can be provided. This allows the surgeon to select an appropriate rod depending on the desired application.

Further modifications of the above described embodiments are also possible. For example, the parts and portions of the different embodiments can be mixed and matched. It also is possible to use any of the described locking members for any of the embodiments of the polyaxial bone anchoring devices described herein. The various pressure members and locking members described before can also be selected and combined.

For the receiving part, other designs are possible, such as a typical top loading design where the bone anchoring element can only be inserted from the top end of the receiving part, or any other bottom loading design where the bone anchoring element can be inserted from the bottom end of the receiving part, as long as the free end of the deformable portions of the pressure member can be supported in the receiving part and the receiving part provides space for the deformation of the deformable portions. The receiving part may be designed such that enlarged pivot angles in a particular direction are possible.

The arms of the pressure member can also have many different shapes as long as a deformation from a first condition to a second configuration is possible. Even one single arm may be sufficient in some embodiments. The arms need not be continuous pieces. For example, it is possible to construct the arms from two substantially rigid levers that are connected via a hinge to form a toggle lever. In this case, the deformation may involve, for example, bringing the toggle lever from a first, angled configuration to a second, more substantially straight configuration.

For the bone anchoring element, different kinds of bone anchoring elements can be used, such as screws, nails, cannulated anchors, hooks, etc. The head and the shank may be constructed from two pieces that connect together. Although the head in the described embodiments is shown to have a spherical segment shape in such a manner that the bone anchoring element is polyaxially pivotable with respect to the receiving part, in some embodiments, the head and/or the receiving part or the pressure member may instead be designed such that pivoting can only take place, for example, in one single plane.

The pressure exerting surface of the pressure member may be in direct contact with the head, or may instead be operatively in contact with the head via, for example, an intermediate part.

In some embodiments, the function of the locking member can also be realized by an instrument. Other kinds of locking members can also be used that are configured to apply similar loads to the pressure member.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A bone anchoring device comprising:

a bone anchoring element comprising a shank for anchoring to a bone and a head;

a receiving part comprising a first end, a second end below the first end, a longitudinal axis extending between the first and second ends, a channel at the first end for receiving a rod, and an accommodation space at the second end for pivotably holding the head of the bone anchoring element;

a pressure member movable in the receiving part, the pressure member comprising a rod engaging surface configured to extend into the channel to engage the rod, the rod engaging surface defining a rod recess for receiving the rod, and a pressure exerting surface configured to directly engage and exert pressure on the head to lock the head in the receiving part, the pressure member further defining a second recess with an opening that is positioned axially higher than a bottom of the rod recess; and a resilient member having a first portion that extends into the second recess of the pressure member and a second portion configured to extend out of the pressure member towards the first end of the receiving part;

wherein when the head, the pressure member, and the resilient member are in the receiving part, the resilient member is adjustable from a first configuration to a second configuration to increase a force exerted by the pressure exerting surface of the pressure member on the head to clamp the head and hold an angular position of the bone anchoring element relative to the receiving part.

2. The bone anchoring device of claim 1, wherein the resilient member is directly accessible from the first end of the receiving part.

3. The bone anchoring device of claim 1, wherein the first portion of the resilient member is fixedly connected to the pressure member.

4. The bone anchoring device of claim 3, wherein the resilient member forms an arm that extends upwardly from the pressure member.

5. The bone anchoring device of claim 1, wherein an axial length of the resilient member is greater at the second configuration than at the first configuration.

6. The bone anchoring device of claim 1, wherein when the resilient member is at the second configuration, the head is locked relative to the receiving part.

7. The bone anchoring device of claim 1, further comprising a locking member that is insertable into the channel and movable in the channel along the longitudinal axis to directly engage the second portion of the resilient member for adjusting the resilient member from the first configuration to the second configuration.

8. The bone anchoring device of claim 1, wherein the resilient member is elastically deformable.

9. The bone anchoring device of claim 1, wherein the resilient member comprises two resilient members positioned on either side of the channel for the rod.

10. The bone anchoring device of claim 1, wherein the opening of the second recess is formed in a topmost end surface of the pressure member.

11. A bone anchoring device comprising:

a receiving part comprising a first end, a second end below the first end, a longitudinal axis extending between the first and second ends, a channel at the first end for receiving a rod, and an accommodation space at the second end for pivotably holding a head of a bone anchoring element; and a pressure member movable in the receiving part, the pressure member comprising a rod engaging surface configured to extend into the channel to engage the rod, a pressure exerting surface configured to directly engage and exert pressure on the head, and an arm on either side of the rod engaging surface that extends towards the first end of the receiving part and that is flexible radially relative to the longitudinal axis;

wherein at least part of the pressure member has a substantially cylindrical profile, wherein at least part of each of the arms extends farther radially from the longitudinal axis than the cylindrical profile to engage the receiving part for holding an axial position of the pressure member, and wherein the pressure member further comprises a projection on either side of the rod engaging surface that is separate from the respective arm and that also extends farther radially from the longitudinal axis than the cylindrical profile.

12. The bone anchoring device of claim 11, wherein each of the projections is formed as a radially extending flange.

13. The bone anchoring device of claim 12, wherein each of the arms extends axially from an upper surface of the respective flange.

14. The bone anchoring device of claim 11, wherein the projection comprises two radially extending corners formed on either side of the respective arm, such that four total corners extend farther radially from the longitudinal axis than the cylindrical profile.

15. The bone anchoring device of claim 11, wherein free ends of each of the arms extends farther radially from the longitudinal axis than the cylindrical profile to engage the receiving part for holding the axial position of the pressure member.

16. The bone anchoring device of claim 11, wherein the at least part of each of the arms is configured to engage a stop on the receiving part to hold the pressure member at an axial position where the pressure exerting surface clamps the head.

17. The bone anchoring device of claim 16, wherein the pressure exerting surface is configured to lock the head relative to the receiving part when the at least part of each of the arms engages the stop.

18. A bone anchoring device comprising: a bone anchoring element comprising a shank for anchoring to a bone and a head; a receiving part comprising a first end, a second end, a longitudinal axis extending through the first end and the second end, a channel at the first end for receiving a rod, and an accommodation space for pivotably holding the head; a pressure member positionable in the receiving part, the pressure member comprising a pressure exerting surface configured to directly engage and exert pressure on the head to lock the head in the receiving part, and a deformable portion; and a locking member configured to be inserted into the channel to move in the channel along the longitudinal axis; wherein when the head and the pressure member are in the receiving part, the locking member is moveable from the first end of the receiving part towards the head, wherein the locking member is configured to directly engage the deformable portion for adjusting the deformable portion from a first configuration to a second configuration to increase a force exerted by the pressure exerting surface of the pressure member on the head to lock the head relative to the receiving part; and wherein when the deformable portion is at the second configuration, the locking member is movable in a direction away from the head and separable from the receiving part while the deformable portion remains at the second configuration and while a position of the pressure member remains substantially constant to keep the head locked.

19. The bone anchoring device of claim 18, wherein a shape of the deformable portion is different in the second configuration compared to the first configuration.

* * * * *